US00PP24167P3

(12) United States Plant Patent

Zaiger et al.

(10) Patent No.: US PP24,167 P3

(45) Date of Patent: Jan. 21, 2014

(54) PEACH TREE NAMED 'SAUZEE GEM'

(50) Latin Name: *Prunus persica*
Varietal Denomination: Sauzee Gem

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 136 days.

(21) Appl. No.: 13/385,865

(22) Filed: Mar. 12, 2012

(65) Prior Publication Data

US 2013/0239267 P1 Sep. 12, 2013

(51) Int. Cl.
*A01H 5/00* (2006.01)

(52) U.S. Cl.
USPC ..... Plt./195

(58) Field of Classification Search
USPC ..... Plt./194, 195
See application file for complete search history.

(56) References Cited

U.S. PATENT DOCUMENTS

| | | | | | |
|---|---|---|---|---|---|
| PP621 | P | * | 3/1944 | Lammerts | Plt./196 |
| PP2,794 | P | * | 2/1968 | Anderson | Plt./192 |
| PP2,964 | P | * | 1/1970 | Merrill | Plt./198 |
| PP5,614 | P | * | 12/1985 | Holtkamp | Plt./267 |
| PP8,034 | P | * | 11/1992 | Zaiger et al. | Plt./195 |
| PP9,883 | P | * | 5/1997 | Zaiger et al. | Plt./195 |
| PP16,179 | P3 | * | 1/2006 | Zaiger et al. | Plt./197 |
| PP21,737 | P2 | * | 3/2011 | Slaughter et al. | Plt./195 |
| PP22,404 | P3 | * | 12/2011 | Zaiger et al. | Plt./194 |

* cited by examiner

*Primary Examiner* — Wendy C Haas

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright growth of tree.
2. Producing peento shaped fruit.
3. Fruit with firm, white flesh, very good flavor and eating quality.
4. Regular and productive bearer of medium to large size fruit.
5. Fruit with an average Brix of 15.1°.

1 Drawing Sheet

Botanical designation: *Prunus persica.*
Variety denomination: 'Sauzee Gem'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

2. Prior Varieties

Among the existing varieties of peach trees, which are known to us, and mentioned herein, 'June Crest' Peach (U.S. Plant Pat. No. 5,614), 'Redwing' Peach (U.S. Plant Pat. No. 621), 'O'Henry' Peach (U.S. Plant Pat. No. 2,964), 'Sugar Giant' (U.S. Plant Pat. No. 8,034), 'Sauzee Queen' Peach (U.S. Plant Pat. No. 16,179), 'May Grand' Nectarine (U.S. Plant Pat. No. 2,794), 'Spring Snow' Peach (U.S. Plant Pat. No. 9,883) and the proprietary peach seedling selection '155LE403' (non-patented).

ORIGIN OF THE VARIETY

The new and distinct variety of peach tree (*Prunus persica*) was originated by us in our experimental orchard located near Modesto, Stanislaus County, Calif. from seed of a first generation cross between our proprietary non-patented peach seedling selection with the field identification number '155LE403' and 'Sauzee Queen' Peach (U.S. Plant Pat. No. 16,179). The seed parent '155LE403' peach (non-patented) originated from crosses between the following varieties; 'May Grand' Nectarine (U.S. Plant Pat. No. 2,794), 'Redwing' Peach (U.S. Plant Pat. No. 621), 'O'Henry' Peach (U.S. Plant Pat. No. 2,964), 'June Crest' Peach (U.S. Plant Pat. No. 5,614) and 'Sugar May' Peach (U.S. Plant Pat. No. 8,034). A large number of seed from this first generation cross were grown and maintained on their own root system and under close and careful observation one such seedling, which is the present variety, exhibited desirable fruit and tree characteristics and was selected in 2003 for asexual propagation and commercialization.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of peach tree (*Prunus persica*) is of large size, vigorous upright growth and a regular and productive bearer of medium to large, white flesh, clingstone fruit. The fruit is further characterized by having an attractive light red skin color, mild, sweet, sub-acid flavor, very good eating quality and being peento in shape. In comparison to its proprietary seed parent '155LE403' peach (non-patented) the fruit of the new variety is peento in shape compared to globose and is approximately 47 days earlier in maturity. In comparison to its pollen parent 'Sauzee Queen' Peach (U.S. Plant Pat. No. 16,179) the fruit of the new variety has a more attractive, red skin color and is approximately 14 days later in maturity. In comparison to the commercial variety 'Spring Snow' Peach (U.S. Plant Pat. No. 9,883) the fruit of the new variety is peento in shape compared to globose and is approximately 7 days later in maturity.

PHOTOGRAPH OF THE VARIETY

The accompanying color photographic illustration shows typical specimens of the foliage and fruit of the present new peach variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 7 year old specimens grown near Modesto, Calif., with color in accordance with Munsell Book of Color.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters the first growing season. Varies slightly with type and fertility of soil, climatic conditions and cultural practices.

*Form*.—Upright, usually pruned to vase shape.

*Branching habit*.—Upright, crotch angle approximately 35°, increases with heavy crop load.

*Productivity*.—Productive, thinning and spacing necessary for desired marketable size fruit. Fruit set varies with climatic conditions during blooming period.

*Bearer*.—Regular, has had adequate fruit set 5 consecutive years. No alternate bearing observed.

*Fertility*.—Self-fertile.

*Density*.—Medium dense, pruning to vase shape desirable for sunlight penetration to enhance fruit color and health of fruit wood.

*Hardiness*.—Hardy in all stone fruit growing areas of California. Tree grown in USDA Hardiness Zone 9. Winter chilling requirement approximately 900 hours at or below 45° F.

Trunk:

*Size*.—Medium, circumference 40.6 cm at 27.9 cm above ground on a 7 year old tree.

*Stocky*.—Medium stocky.

*Texture*.—Medium shaggy, becoming rougher with age.

*Color*.—Varies from 10YR 3/2 to 2.5Y 3/4.

Branches:

*Size*.—Medium. Average circumference 17.5 cm at 1.1 meters above ground. Crotch angle approximately 35°, increases with heavy crop load.

*Surface texture*.—New growth relatively smooth. Mature growth medium rough, roughness increases with age.

*Lenticels*.—Average number 25 in a 25.8 sq cm section. Average length 5.0 mm. Average width 2.4 mm. Color varies from 10YR 2/2 to 2.5Y 3/4.

*Color*.—New growth 5GY 6/6. Mature growth 7.5YR 3/6, varies with age of growth.

Leaves:

*Size*.—Large. Average length 167.9 mm. Average width 50.4 cm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slight indentation over midrib and leaf veins. Lower surface relatively smooth, except for small ridges created by midrib and pinnate venation. Both surfaces glabrous.

*Petiole*.—Average length 10.8 mm. Average width 2.1 mm. Longitudinally grooved. Surface — glabrous. Color — 5GY 6/6.

*Glands*.—Reniform. Size — small. Average length 0.6 mm. Average diameter 0.4 mm. Average number 2, varies from 1 to 3. Located primarily on base of leaf blade, upper portion of petiole. Color — 5GY 6/6.

*Stipules*.—Average number 2. Average length 7.8 mm. Edges — ciliate. Color varies from 2.5GY 5/8 to 5GY 5/8.

*Color*.—Upper surface varies from 10GY 3/4 to 10GY 4/4. Lower surface varies from 2.5G 4/4 to 5G 4/4. Midvein color varies from 5GY 8/2 to 7.5GY 7/4.

Flower buds:

*Size*.—Medium to large. Average length 21.8 mm. Average diameter 11.7 mm.

*Hardiness*.—Hardy with respect to California winters.

*Form*.—Plump, conical, becoming elongated before opening.

*Pedicel*.—Average length 4.9 mm. Average width 1.5 mm. Color varies from 5GY 7/6 to 5GY 7/8.

*Color*.—Varies from 7.5RP 7/8 to 5RP 8/6.

Flowers:

*Blooming period*.—Date of First Bloom Mar. 1, 2011. Date of Petal Fall Mar. 11, 2011, varies slightly with climatic conditions.

*Size*.—Large, showy. Average height 24.6 mm. Average diameter 45.7 mm.

*Petals*.—Normally 5, alternately arranged to sepals. Size — large. Average length 22.7 mm. Average width 20.9 mm. Form — ovate, narrows at point of attachment. Margin — sinuate. Both upper and lower surfaces glabrous. Color varies from 5RP 9/2 to 5RP 6/10.

*Sepals*.—Normally 5, alternately arranged to petals. Size — large. Average length 7.0 mm. Average width 5.6 mm. Shape — ovate. Margin — entire. Upper surface glabrous, lower surface pubescent. Color — upper surface varies from 5GY 6/8 to 5R 3/6. Lower surface varies from 5R 3/4 to 5R 2/6.

*Stamens*.—Average number per flower 41. Average filament length 19.3 mm. Filament color varies from 5RP 9/12 to 5RP 7/8. Anther color varies from 7.5R 4/12 to 7.5Y 8/8.

*Pollen*.—Self fertile. Color varies from 5Y 8/10 to 5Y 7/12.

*Pistil*.—Normally 1. Surface — pubescent. Average length 17.9 mm. Position of stigma approximately 4.8 mm above anthers. Color varies from 2.5GY 9/4 to 2.5GY 8/6.

*Fragrance*.—Heavy aroma.

*Color*.—Varies from 5RP 8/6 to 7.5RP 9/2.

*Number flower per flower bud*.—One.

*Pedicel*.—Average length 5.0 mm. Average width 2.2 mm. Color varies from 2.5GY 7/8 to 5GY 7/6.

Fruit:

*Maturity when described*.—Firm ripe.

*Date of first picking*.—Jun. 2, 2011.

*Date of last picking*.—Jun. 10, 2011, varies slightly with climatic conditions.

*Size*.—Medium to large. Average diameter axially 34.3 mm. Average transversely in suture plane 72.6 mm. Average weight 139.2 grams, varies slightly with fertility of the soil, amount of thinning and climatic conditions.

*Form*.—Peento shape.

*Suture*.—Distinct, extends from base to apex.

*Ventral surface*.—Slightly lipped, well sealed.

*Apex*.—Retuse.

*Base*.—Retuse.

*Stem cavity*.—Rounded to slightly elongated in suture plane. Average depth 4.3 mm. Average diameter 12.2 mm.

Stem:

*Size*.—Small. Average length 9.0 mm. Average diameter 3.2 mm.

*Color*.—Varies from 10Y 6/8 to 2.5GY 6/6.

Flesh:

*Ripens*.—Relatively evenly, slightly earlier at the apex.

*Texture*.—Firm, meaty.

*Fibers*.—Few, small, tender.

*Firmness*.—Firm.

*Aroma*.—Heavy aroma.

*Amydgalin*.—Undetected.

*Eating quality*.—Very good.

*Flavor*.—Very good, sweet, sub-acid flavor.

*Juice*.—Moderate amount, enhances flavor.

*Brix*.—Average Brix 15.1°, varies slightly with amount of fruit per tree and climatic conditions.

*Color*.—Varies from 7.5Y 8/2 to 10Y 8/2.

*Pit cavity*.—Average length 13.2 mm. Average width 19.0 mm. Average depth 9.2 mm. Color 5Y 7/4.

Skin:

*Thickness*.—Medium.

*Surface*.—Smooth.

*Pubescence*.—Moderate amount, short in length.

*Tendency to crack*.—None.

*Color*.—Ground color varies from R-Y 9/5Y to 2.5Y 9/2. Overspread with 5R 4/8 to 5R 4/6.

*Tenacity*.—Tenacious to flesh.

*Astringency*.—None.

Stone:

*Type*.—Clingstone.

*Size*.—Small to medium. Average length 13.1 mm. Average width 18.4 mm. Average thickness 19.5 mm.

*Form*.—Peento shape, resembling shape of fruit.

*Base*.—Flat to slightly rounded.

*Apex*.—Slightly rounded.

*Surface*.—Pitted throughout.

*Sides*.—Unequal, one side extending further from suture plane.

*Ridges*.—Small, narrow ridges extending from base toward apex.

*Tendency to split*.—Slight to none.

*Color*.—Varies from 10YR 6/4 to 2.5Y 7/4 when dry.

Kernel:

*Size*.—Small. Average length 8.3 mm. Average width 9.3 mm. Average thickness 7.2 mm.

*Form*.—Round to ovoid.

*Viability*.—Non-viable, incomplete embryo development.

*Skin*.—Color varies from 5Y 9/2 to 7.5YR 9/2.

Use:

*Dessert*.—Market — local and long distance.

Keeping quality: Good, held firm in cold storage for two weeks at 38° to 42° F. without internal breakdown or appreciable loss of flavor.

Shipping quality: Good, minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

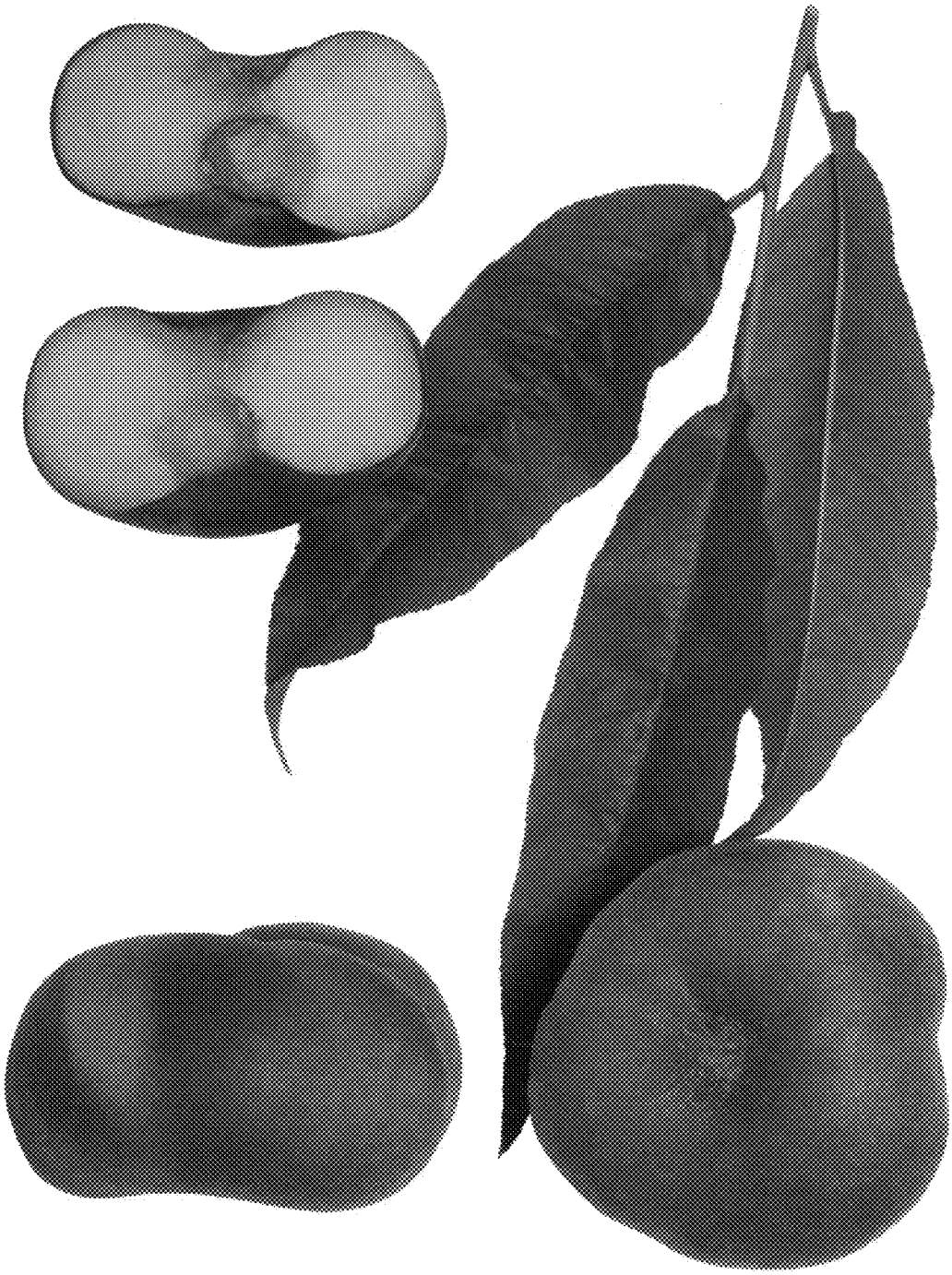

* * * * *